United States Patent [19]

Passafiume et al.

[11] 4,409,049
[45] Oct. 11, 1983

[54] METHOD AND APPARATUS FOR EFFECTING INTERMITTENT SECUREMENT OF A STRETCHED ELASTIC MEMBER TO A MOVING WEB

[75] Inventors: Anthony Passafiume, Burbank; Heinz A. Pieniak, Chicago, both of Ill.

[73] Assignee: Johnson & Johnson Baby Products Company, New Brunswick, N.J.

[21] Appl. No.: 253,419

[22] Filed: Apr. 13, 1981

[51] Int. Cl.³ .................... B32B 31/10; A61F 13/16
[52] U.S. Cl. .................................. 156/164; 156/179; 156/229; 156/291; 156/301; 156/436; 156/522; 156/552; 156/553; 156/555

[58] Field of Search ............... 156/164, 301, 302, 300, 156/229, 280, 281, 287, 522, 552, 553, 555, 548, 484, 436, 176, 178, 179; 128/287, 284

[56] References Cited

U.S. PATENT DOCUMENTS

| | | | |
|---|---|---|---|
| 4,081,301 | 3/1978 | Buell | 156/164 |
| 4,293,367 | 10/1981 | Klasek | 156/164 |
| 4,300,967 | 11/1981 | Sigl | 156/164 |

*Primary Examiner*—Michael W. Ball
*Attorney, Agent, or Firm*—Martha A. Michaels

[57] ABSTRACT

Method and apparatus for continuously attaching an elastic member to discrete portions of a moving web to impart an elasticized character to predetermined portions of the web while preserving the inelastic character of the other portions of the web.

16 Claims, 9 Drawing Figures

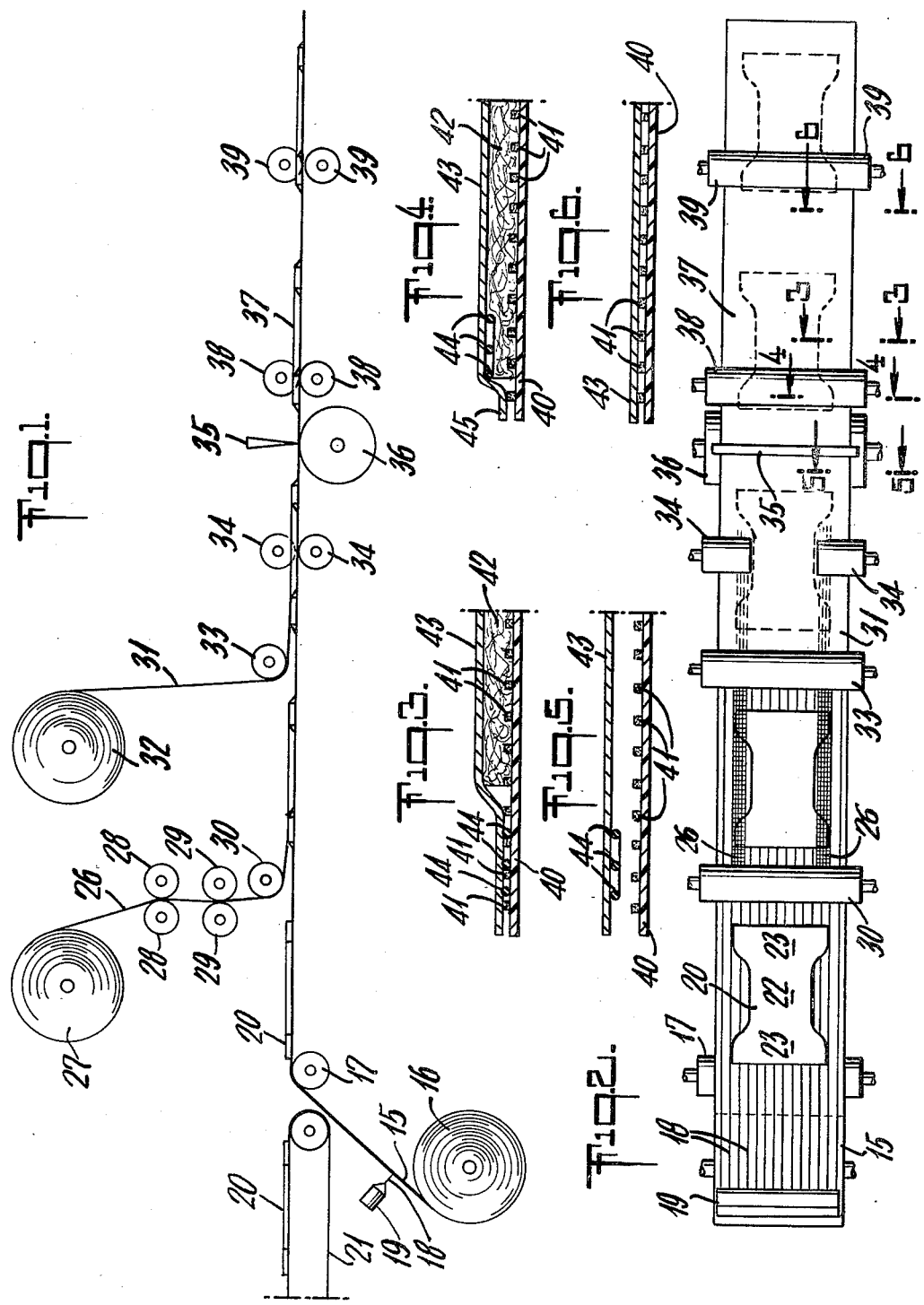

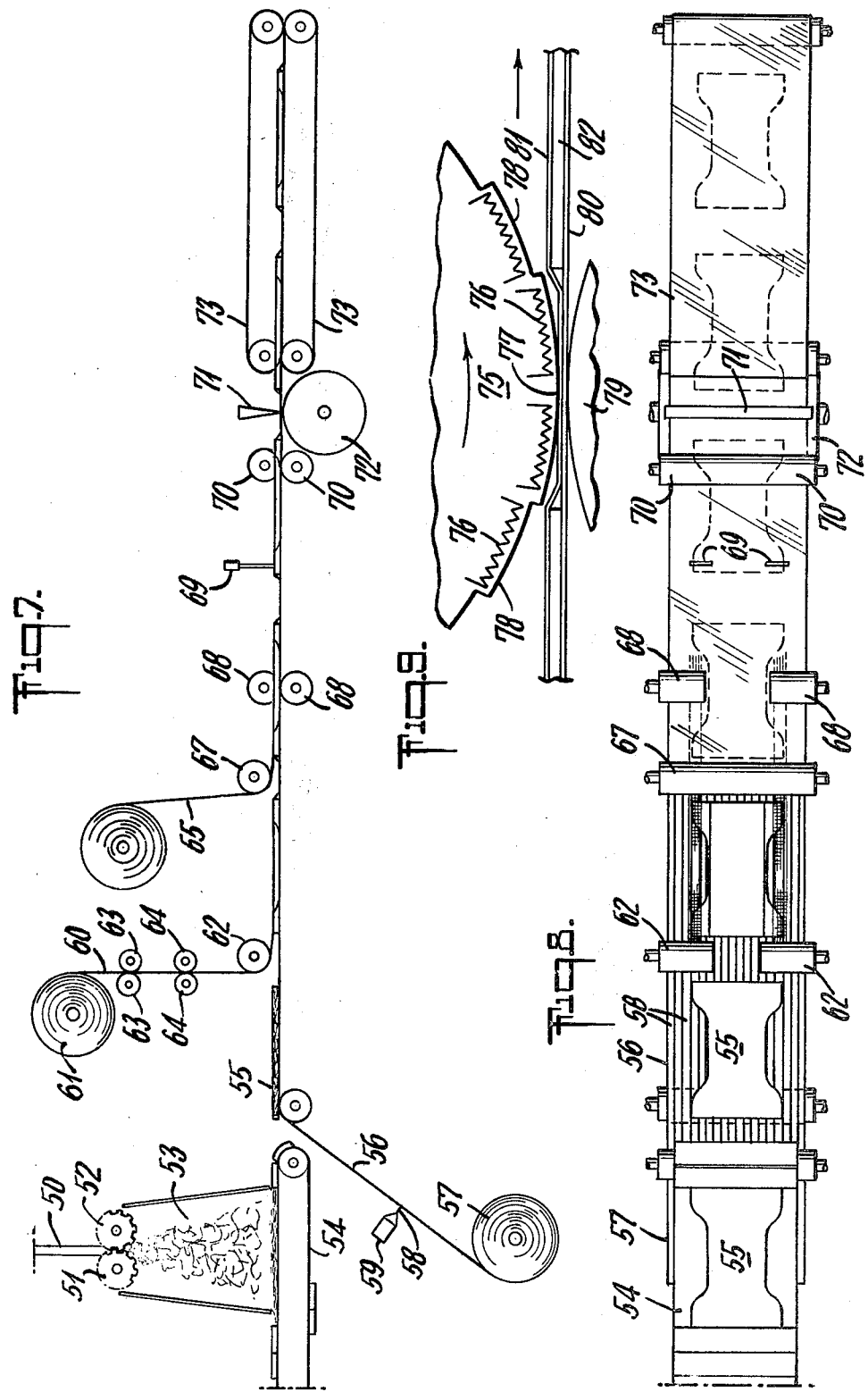

METHOD AND APPARATUS FOR EFFECTING INTERMITTENT SECUREMENT OF A STRETCHED ELASTIC MEMBER TO A MOVING WEB

TECHNICAL FIELD

This invention relates to method and apparatus for intermittently securing a moving elastic member or element to a moving web or disposable diaper components and the like.

BACKGROUND OF THE INVENTION

Methods are known for fixing an elastic member or element such as an elastomeric band or ribbon to a flexible substantially inelastic web of material defining clothing or components thereof including briefs, panty briefs, disposable diapers and the like.

Methods are known for applying an elastic element to a continuously moving web. U.S. Pat. No. 3,828,367 to Bourgeois discloses a method for securing a stretched elastic element to a non-elastic fabric web and maintaining the assembled element on a web in a stretched condition until cut transversely in the direction of travel to produce separated panels. The apparatus is disclosed as including a rotating cylinder with a curved guide for imparting a non-linear configuration to the elastic element so that the ribbon follows a pre-determined contour of the non-elastic fabric.

U.S. Pat. No. 4,081,301 to Buell cites other prior art patents showing ways in which an elastic ribbon is joined to a moving web of material. The Buell patent itself discloses a method and apparatus for continuously attaching discrete lengths of elastic ribbon to a moving web. The elastic ribbon is fed in a stretched condition to the web and the elastic ribbon is intermittently secured to predetermined regions of the web while so stretched. Subsequently, the web and elastic ribbon are transversely cut in an area where the elastic ribbon is not secured to the web. This step forms severed unadhered portions of elastic at both ends of each discrete length of said elastic ribbon adhered to the web. The severed unadhered ends of the elastic ribbon are allowed to relax and contract to their unstretched state.

With the method disclosed in the above-discussed Buell patent, it is important that the moving elastic ribbon be secured to the moving web precisely at predetermined regions of the web and that the moving elastic ribbon and moving web be severed precisely in the region where the elastic ribbon is not adhered to the web. This requires that the adhesive which is applied intermittently to the stretched elastic ribbon be precisely controlled for exact deposition combined with precisely controlling the placement of that exact area having adhesive thereon on the moving member. For example, if the adhesive is not put on correctly and the adhesive spaced correctly, the stretched elastic ribbon would be accidentally adhered beyond the pre-determined region and when then severed, the elastic ribbon would contract to impart an elasticized character beyond the desired pre-determined region. Thus, the securing mechanism such as the adhesive applicators, heat sealing devices, must be carefully controlled and actuated to effect securement precisely in the desired regions. With the very high speed manufacturing operations necessary for disposable product manufacture, accurate control of such mechanisms becomes difficult. Further, the securing mechanism is a movable device, and stresses imparted to the moving securing mechanism increase owing to the more rapid acceleration and deceleration which necessarily occur in high-speed stop and start operations. Furthermore, the intermittent application of either a liquid or semi-solid adhesive in fine lines through small orifices or nozzles is difficult. The continual stopping and starting of the ejection of adhesive through the nozzles causes the nozzles to clog or stop-up during use, thus causing considerable down-time and loss of production.

In order to avoid the problems of precisely and accurately registering ribbon securing mechanisms in a high-speed operations, the imposition of high stress on moving mechanical members and the possible clogging of nozzles, it would be desirable to provide a method and apparatus in which the securing mechanism or adhesive is disposed continuously and uniformly throughout the operation. With such a method, the securing means is operated along the entire length of the elastic member so as to avoid the problems associated with high-speed cyclic operation.

Further, in accordance with our new and improved method, the relative positioning of the various components making up a stretch disposable diaper, that is, one that has elastic on the leg portion of the diaper, is no more complicated than the problem of the relative positioning of the components of a standard or flat disposable diaper. In its broadest aspects, the invention of our new and improved method for inserting elastic members into disposable diapers is to control the shape of the absorbent panel and thereby control the positioning and securement of the elastic member in the diaper.

SUMMARY OF THE INVENTION

According to the present invention, a method and apparatus is provided for securing an elastic member to a continuously moving flexible, generally inelastic, web of material, such as material defining disposable diaper components and the like, to impart a stretchable characteristic at pre-determined portions of the components while preserving in other portions the generally inelastic characteristic of the components. A web of inelastic material is moved along a path to a securement zone. Securement means are uniformly applied to a surface of said moving inelastic web. Spaced apart, shaped absorbent panels are placed on the securement means on the surface. The absorbent panels have a narrowed central portion and wider end portions at both ends of the panel to form ears extending beyond the longitudinal edges of the central portion of the panel. Elastic members in a stretched condition are continuously fed along each longitudinal edge. In a preferred embodiment, the elastic members are substantially adjacent and parallel to the longitudinal edge of the central portion of the absorbent panel. The stretched elastic members are disposed on the securement means in the central portion adjacent the panel and over the ears at the ends of the panel so that they are not in contact with the securement means at the opposite ends of the panel. A second inelastic web is fed to the top surface of the panel and compressed at least along the longitudinal edges of the central portion of the panel to secure the two webs together adjacent that portion of the panel. The laminate may then be severed between adjacent panels and if desired, the end margins of the laminate may now be compressed to produce a plurality of individual disposable diapers.

In one embodiment of the method of the present invention, a continuous impermeable backing material is continuously fed to a securement zone. Adhesive material is uniformly applied to one surface of said impermeable backing and spaced apart shaped absorbent panels are placed on the adhesive. The backing extends beyond the side edges of the panel to form longitudinal side margins. The absorbent panels have an hour-glass shape with a narrowed central portion and wider end portions at both ends of the panel. Stretched, reticulated, elastic members are continuously fed along each longitudinal side margin of the backing with the member disposed on the adhesive in the central portion adjacent the panel and over the ears at the ends of the panel and, therefore, not in contact with the adhesive at those ends. A continuous permeable facing material is fed to the top surface of the panels. The facing material is substantially co-extensive with the backing material. The longitudinal side margins of the backing and facing are compressed together adjacent the edges of the panel in the central portion thereof. The ends of the elastic may be rendered inelastic and the laminate compressed and severed between panels to form individual laminated products or the elastic may be severed between central portions of adjacent panels and allowed to retract and the laminate compressed and severed between panels to form individual products.

The apparatus of the present invention includes means for applying adhesive to a moving web and means for feeding spaced apart absorbent panels to said adhesive carrying surface. The apparatus of the present invention also includes means for feeding stretched elastic members adjacent the absorbent panels and means for laminating a second web to the first web and securing this laminate into a plurality of individual laminated products.

Thus, it is seen that the present invention yields desirable and beneficial results. Results which are not only new and different, but which also provide a substantial improvement over the prior art.

Numerous other advantages of the present invention will become readily apparent in the following detailed description of the invention and of the various embodiments thereof as well as from the claims and the accompanying drawings.

BRIEF DESCRIPTION OF THE DRAWINGS

FIG. 1 is a side elevational schematic view of one form of apparatus for carrying out the method of the present invention.

FIG. 2 is a top plan view of the apparatus depicted in FIG. 1;

FIG. 3 is an enlarged cross-sectional view taken at line 3—3 of FIG. 2;

FIG. 4 is an enlarged cross-sectional view taken at line 4—4 in FIG. 2;

FIG. 5 is an enlarged cross-sectional view at line 5—5 in FIG. 2;

FIG. 6 is an enlarged cross-sectional view at line 6—6 of FIG. 2;

FIG. 7 is a side elevational schematic view of another form of apparatus for carrying out the method of the present invention;

FIG. 8 is a top plan view of the apparatus depicted in FIG. 7; and

FIG. 9 is an enlarged cross-sectional view of one form of apparatus for rendering portions of thermoplastic film elastic members inelastic.

Referring to FIGS. 1 and 2 of the drawings, a suitable backing material 15 is fed from a supply roll 16 to a conveying roller 17. Adhesive 18 is extruded through a plurality of nozzles 19 onto the backing material. A plurality of absorbent panels 20 are fed from a conveyor 21 to the adhesive on the backing material.

The absorbent panels are spaced apart an appropriate distance so as to produce individual disposable diapers. The absorbent panels have a general hourglass shape; that is, the center portion 22 is narrower than the two end portions 23 and 24 of the panel. The center portion of the pad fits between the legs of the wearer while the end portions fit about the waist of the wearer.

A pair of elastic members 26 are fed from suitable supply rolls 27 through a first set of nip rolls 28 then to a second set of nip rolls 29. The second set of nip rolls has a peripheral linear speed greater than the first set of nip rolls to stretch the elastic member. The elastic member then passes about a guide roller 30 and each elastic member is positioned along the longitudinal edge of the center portion of the absorbent panel. The elastic member contacts the adhesive on the backing, adjacent the center portion of the panel, and is disposed on top of the panel at the end portions thereof. In a preferred embodiment of the present invention as shown in FIG. 2, the elastic member is reticulated or has apertures in it so that the adhesive will bleed through the apertures of the elastic member and adhere the backing to the facing to be subsequently placed on the backing. After the elastic members have been positioned on the backing, an appropriate facing material 31 is fed from a supply roll 32 about a guide roller 33 to the upper surface of the backing and panels. The portion of the laminate adjacent the center portion of the panel is compressed by the laminating rollers 34 to adhere the facing to the backing and to secure the elastic member therebetween. The laminating rollers are operated intermittently so that they only compress the laminate adjacent the center portion of the panel and they do not compress the wider end portions of the panel or between panels. If it is desired not to use intermittently operating rolls, larger rolls may be used with a gap left in the periphery of one or both of the rolls so as not to compress at the ends of the panel or between panels. A cutting knife 35 cooperating with an anvil roll 36 severs the laminate at the mid-portion between absorbent panels to form a plurality of individual disposable diapers 37. The end portions of the diapers, that is, the portions where there is only facing and backing materials and not an absorbent panel, are then laminated to one another by laminating rollers 38. Again, these laminating rolls are operated intermittently so as not to compress the panel. The finished diapers are then carried forward by conveying rolls 39 for appropriate folding and packaging.

As is shown in FIG. 3, in the portion of the diaper at the narrowed section of the panel, the diaper comprises backing 40 which is adhered by the adhesive 41 to the absorbent panel 42 with an upper facing material 43. At the outside edge of the diaper in this section, there is the backing 40 which is adhered to the facing material 43 through the apertures or reticulations in the reticulated elastic member 44.

As is shown in FIG. 4, at the wider ends of the absorbent panel 42, the backing 40 is adhered to the absorbent panel by the adhesive 41 substantially across its entire width. The elastic member 44 is on the upper surface of the absorbent panel and not adhered in this area. The facing 43 overlies the absorbent batt and the elastic member and is adhered along its outer longitudinal edge 45 to the backing 40.

As is shown in FIG. 5, at the ends of the laminate, prior to severing, the backing 40 carries adhesive lines 41 with the facing 43 and the elastic member 44 spaced from the adhesive. In FIG. 6, after the diaper has been severed, and the elastic member allowed to retract from the end portions and the end portions compressed, the diaper has backing 40 adhered to facing 43 by the adhesive lines 41.

Referring to FIGS. 7 and 8 of the drawings, there is shown another embodiment of apparatus for carrying out the process of the present invention. Referring to FIG. 7, a pulp board 50 is fed to a grinding mill which comprises a pair of tooth rolls 51 and 52 which separate and individualize the wood pulp fibers from the pulp board. The individualized fibers are air-conveyed 53 to a foraminous screen 54. The screen is blocked off in the desired shape of the panel; that is, the shape of the panel is foraminous on the screen while the remaining portion of the screen is solid.

The individual pulp panels 55 once formed are fed to a polyethylene backing film 56. The polyethylene film is provided from a suitable supply roll 57 and has on its surface a series of adhesive lines 58 applied by appropriate nozzles 59. The pulp panels are applied to the surface of the polyethylene on which the adhesive lines are applied. A pair of elastic members 60, and in this embodiment they are solid thermoplastic film members, are fed along each longitudinal edge of the pulp panel. The pulp panel has a shape wherein the center portion is narrowed as compared to the end portions of the panel. The elastic members are fed from supply rolls 61 and are stretched by two pairs of rolls. The first pair 63 takes the member from the supply roll, and the second pair 64, travelling at a faster peripheral linear speed than the first pair, stretches the elastic member the desired amount. The stretched members pass about guide roll 62 so as to abut or be substantially adjacent the longitudinal edges of the center portion of the panel and be disposed over the wider end portions of the panel. A suitable facing material 65 is fed from a supply roll to the top surface of the panels and elastic members. The facing is fed around a guide roll 67 onto the surface. A pair of laminating rolls 68 adjacent each edge of the laminate apply pressure to the facing and backing and the elastic member to secure the elastic member between the facing and backing. The laminating rolls are gapped, i.e., there is a groove or indentation on the periphery of at least one of the rolls so that pressure is applied to the facing and backing only adjacent the narrow center portion of the panel and not at the end portions. In this embodiment, the elastic member being a thermoplastic elastomeric film, is severed by a hot knife 69 at the ear or the wider portion of the pulp panel. By placing the thermoplastic elastic member over the ear of the panel, the panel acts as a "heat sink" and allows the elastic member to be severed by applying heat to it at that portion of the member lying on the panel. The panel absorbs the heat and acts as an insulator so there is no detrimental effect or damaging of the thermoplastic, impermeable film backing. The heat severs the elastic member and allows it to contract at the severed ends to render the end effectively inelastic. The laminate is compressed and secured together between absorbent panels by a pair of intermittently operating laminating rolls 70. The laminate is severed between adjacent panels by the knife 71 and anvil roll 72 to form individual disposable diapers. The diapers are conveyed away by conveyors 73 to suitable folding and stacking mechanisms as is well known in the industry. In this embodiment the laminating of the end portions maybe accomplished before the laminate is severed if desired.

In FIG. 9, there is depicted another apparatus for rendering thermoplastic elastic film members effectively inelastic. In this embodiment, a heated rotary roll 75 has a two-section, stepped-down periphery. Heating coils 76 are disposed in the two outermost peripheral areas 77 and 78 of the roll. The heated roll cooperates with a back-up roll 79. The diaper assemblies pass between the heated rotating roll and the back-up roll with the film backing material 80 adjacent the surface of the back-up roll. The outermost heated periphery 77 of the heated rotating roll is synchronized to contact the facing 81 between adjacent absorbent panels 82 and the stepped-down heated portion 78 contacts the facing at the ears or wider portions of the absorbent panels. The heated roll applies heat to the facing and to the thermoplastic film elastic member in the areas of contact and the heat sets the elastic member and renders that area effectively inelastic.

The absorbent panels which are useful in the process of the present invention are those absorbent panels which have narrowed central portions and wider edge portions so that they form ears at each end of the panel. It is this ear portion combined with the narrowed central portion which allows the elastic member to be placed adjacent the panel in the central portion and over the ears so that the elastic member, in accordance with the process of the present invention, only becomes functional in the desired area; that is, the area that is to become the leg-encircling area of the diaper. There are many ways of preforming panels in desired shapes. Suitable techniques for preforming such panels are disclosed and described in commonly assigned U.S. Pat. No. 4,216,687 and co-pending patent application Ser. No. 51,562 filed June 25, 1979 now U.S. Pat. No. 4,279,369. Other techniques are those described in conjunction with FIGS. 7 and 8 herein.

As previously mentioned in a preferred embodiment, the panel is shaped so that the narrowed central portion has parallel longitudinal edges and the elastic members are laid adjacent and parallel to these longitudinal edges. In other embodiments, the panel may have a narrowed central portion without parallel longitudinal edges and the elastic members are laid adjacent to longitudinal edges but not parallel thereto.

The absorbent panels may be made from various materials; for example, a multiplicity of creped cellulose wadding, or fluff cellulosic fibers of wood pulp fibers or other absorbent materials. The preferred embodiment panels are those made from wood pulp fibers, that is, the air-laid material and generally they have a basis weight of approximately 0.3 to 0.35 grams per square inch. The basis weight, of course, will vary depending on the size and shape of the diaper, and the use to which it is to be put; to wit, Daytime, Nighttime, Toddler, and the like.

Broadly, the elastic members useful in accordance with the present invention may be made from materials having elongation of from 20 to 100% and preferably from about 50 to 500% with recoveries in the range of 20 to 100% and preferably from 70 to 100%. The material should have a force to stretch it 100% of from 30 to 2000 grams. A specifically suitable elastic member is that disclosed in co-pending commonly assigned patent application. U.S. Ser. No. 134,369 filed Mar. 27, 1980.

The elastic members may be made from rubber or various synthetic elastomeric materials, preferably they are made from the thermoplastic elastomeric materials as are more fully disclosed and described in the co-pending commonly assigned patent application U.S. Ser. No. 134,369 filed Mar. 27, 1980. Materials may be anywhere from ¼ to 1½ inch in width or even wider and may be apertured or solid as desired. In a preferred embodiment, the material is an apertured or reticulated elastomeric material with a ¾ inch width.

The elastic members may be secured in the diapers by ultrasonic bonding, heat sealing or by using any of the well known hot melt or liquid adhesive materials available from the adhesive industry, and which are compatible with the elastic member being used.

Facing materials which may be used with the disposable products of the present invention may be non-woven webs made of a mixture of fibers consisting of predominantly of inexpensive short cellulosic fibers, such as short wood pulp fibers, or cotton linters in amounts of 75% to 98%, the balance being textile length fibers such as rayon, as described in U.S. Pat. No. 3,663,348 to Liloia, et al. Other facing materials which are suitable for use in disposable diapers of this invention can have fabric weights in the range of about 0.25 to 5 ounces per square yard and densities of less than 1.5 grams/cc., generally in the range of from 0.2 to 1 gram/cc. The dry strength of the facing sheet for a fabric having a weight of about 1.5 ounces per square yard is at least 1.5 lbs. per inch of width in the machine direction and at least 0.1 lb. per inch of width in the cross direction. Such fabrics have good elongation, good loft and drape characteristics. Facings may also be made of an apertured non-woven fabric which is formed, for example, in accordance with the teachings of commonly assigned U.S. Pat. Nos. 2,862,251, 3,081,514, and 3,081,515. Furthermore, facings may also be made from other types of fabric such as those disclosed and described in U.S. Pat. No. 3,485,706 to Evans. Such facings can be made of naturally occurring fibers, artificial fibers, synthetic fibers or blends thereof. Typical facing sheets made of polyester type fibers may have a weight of about 0.75 ounces per square yard. The facing may be the same size as and coterminous with the backing or, alternatively, the facing may be wider than the backing and have its side edges inwardly folded so that the facing is coterminous with the backing as is shown in FIG. 3 of U.S. Pat. No. 3,612,055.

In the latter case, the elastic members may be secured above the inwardly folded side edges of the facing. In addition, facings may be made from non-apertured material such as non-woven isotropic webs or apertured polyolefin or polyester films having a desired moisture permeability. In all of the aforementioned facings, the material should be relatively hydrophobic so as to retard wicking with the facing.

Suitable backing material for the disposable undergarments embodying the present invention can be an opaque polyolefin, for example, polyethylene about 0.001 inch thick. Another suitable material for this purpose is polyethylene terephthlate having a thickness of about 0.005 inch.

The foregoing description and the drawings are illustrative and are not to be taken as limiting. Still other variations and modifications are possible without departing from the spirit and scope of the present invention.

What is claimed is:

1. A method for continuously attaching an elastic member to discrete portions of a moving web to impart an elasticized character to pre-determined portions of the web while preserving the inelastic character of the other portions of the web, said method comprising the steps of:
   (a) moving a first substantially inelastic web;
   (b) applying a plurality of continuous adhesive lines to one surface of said first moving inelastic web;
   (c) feeding spaced apart absorbent panels, each panel having a narrowed center portion and wider end portions, to the surface of the moving web on which the adhesive has been applied;
   (d) feeding a pair of stretched elastic members over at least one adhesive line along the longitudinal edges of said absorbent panel, with the members adjacent the edge of the panel along the narrowed center portion and overlying the panel at its wider end portion;
   (e) feeding a second substantially inelastic web to the top surface of the absorbent panel;
   (f) laminating the second inelastic web and the first inelastic web together at the edge of the panel to bond the elastic member in place along the narrowed center portion; and
   (g) severing the laminate between adjacent absorbent panels whereby the elastic member relaxes in the remaining unbonded portion to produce a plurality of individual laminated products.

2. The method according to claim 1 wherein the severed laminated products are further laminated at the end portions of the product.

3. The method according to claim 1 wherein the elastic members are severed at a wider end portion of the panel, the first inelastic web and the second inelastic web are laminated between adjacent absorbent panels, and the laminate is severed between adjacent panels to produce a plurality of individual laminated products.

4. The method according to claim 1 wherein the adhesive is applied to the surface of the first inelastic web in a plurality of longitudinally extending parallel lines.

5. The method according to claim 4 wherein the elastic member is an apertured member and the first inelastic web is laminated to the second inelastic web in the apertures of the elastic member.

6. The method according to claim 1 wherein the elastic members are fed adjacent and parallel to the edge of the narrowed center portion of the panel.

7. The method according to claim 1 wherein the first inelastic web is an impervious film member and the second inelastic web is a pervious fabric member.

8. A method of attaching elastic members between first and second relatively inelastic webs to impart elasticity to selected portions of the resulting laminate comprising:
   (a) continuously applying adhesive to the surface of the first inelastic web;
   (b) depositing shaped absorbent panels in spaced relationship on said adhesive, the panels having a narrowed central portion and wider end portions, the first inelastic web and the adhesive extending outboard of the panel along the entire length of both longitudinal edges of the panel;
   (c) feeding an elastic member in a stretched condition to the surface of the web carrying the adhesive so that the elastic member overlies the adhesive adjacent the central portion of the panel and overlies the panel at the end portions thereof;

(d) placing the second inelastic web on top of said batt and said elastic member in contact with adhesive exposed outboard of the elastic member;

(e) applying pressure to the laminate adjacent the longitudinal edges of the narrowed central portion of the panel to secure the first web to the second web and the elastic member to the first web; and (f) severing the laminate between adjacent absorbent panels whereby the elastic member relaxes in the remaining unbonded portion and applying pressure to the laminate in the area between absorbent panels to adhere the first web to the second web in that area.

9. The method according to claim 8 wherein the elastic member is rendered inelastic in the area that overlies the end portions of the panel before the laminate is severed between adjacent absorbent panels.

10. The method according to claim 8 wherein the elastic member is severed in the area that overlies an end portion of the panel before the laminate is severed between adjacent absorbent panels.

11. Apparatus for continuously attaching an elastic member to discrete portions of a moving web to impart an elasticized character to the outer portions of the web comprising:

(a) means for moving a first inelastic web;

(b) means for continuously applying adhesive to a surface of said first web;

(c) means for feeding shaped absorbent panels having a narrowed center portion and wider end portions in spaced apart relationship to the surface of the first web to which the adhesive is applied;

(d) means for feeding a stretched elastic member over the adhesive along the longitudinal edge of the center portion of the panel and over the wider end portions of said panel;

(e) means for feeding a second web on top of said panel and said elastic member;

(f) means for laminating the second web to the first web adjacent the center portion of the absorbent panel; and (g) means for severing the first and second webs between adjacent absorbent panels whereby any remaining stretched unadhered portions of the elastic member relax.

12. Apparatus according to claim 11 which includes means for severing the elastic member at the wider end portion of the panel.

13. Apparatus according to claim 12 wherein the elastic member is thermoplastic and the means for severing the member is a hot knife.

14. Apparatus according to claim 11 which includes means for laminating the second web to the first web between adjacent absorbent panels.

15. Apparatus according to claim 11 wherein the means for laminating the second web to the first web adjacent the center portion of the absorbent panel is a pressure nip formed between a pair of rolls and means for intermittently opening and closing the pressure nip in synchronization with the shape of the absorbent panel.

16. Apparatus according to claim 15 including a second pressure nip formed between a second pair of rolls and means for intermittently opening and closing said second pressure nip in synchronization with the spacing between absorbent panels to laminate the second web to the first web between adjacent absorbent panels.

* * * * *